US010210610B2

(12) United States Patent
Iwasaki et al.

(10) Patent No.: US 10,210,610 B2
(45) Date of Patent: Feb. 19, 2019

(54) IMAGE PROCESSING APPARATUS FOR GENERATING COMBINED IMAGE SIGNAL OF REGION-OF-INTEREST IMAGE SIGNAL AND SECOND IMAGE SIGNAL, THE REGION-OF-INTEREST IMAGE SIGNAL BEING GENERATED BASED ON BLANK PORTION AND INITIAL REGION-OF-INTEREST OF FIRST IMAGE SIGNAL

(71) Applicant: OLYMPUS CORPORATION, Tokyo (JP)

(72) Inventors: Tomoki Iwasaki, Fuchu (JP); Tatsuhiko Suzuki, Hino (JP); Susumu Hashimoto, Hachioji (JP); Yuji Kutsuma, Kokubunji (JP); Toshihiro Hamada, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 154 days.

(21) Appl. No.: 15/369,033

(22) Filed: Dec. 5, 2016

(65) Prior Publication Data
US 2017/0084031 A1  Mar. 23, 2017

Related U.S. Application Data

(63) Continuation of application No. PCT/JP2015/071511, filed on Jul. 29, 2015.

(30) Foreign Application Priority Data

Jul. 30, 2014 (JP) .................................. 2014-154914

(51) Int. Cl.
G06K 9/00 (2006.01)
G06T 7/00 (2017.01)
(Continued)

(52) U.S. Cl.
CPC .......... *G06T 7/0012* (2013.01); *A61B 1/0005* (2013.01); *A61B 1/00009* (2013.01);
(Continued)

(58) Field of Classification Search
None
See application file for complete search history.

(56) References Cited

U.S. PATENT DOCUMENTS 5,091,964 A * 2/1992 Shimomura ....... H04N 1/40062
358/462
5,268,967 A * 12/1993 Jang ...................... G06T 7/0012
382/132

(Continued)

FOREIGN PATENT DOCUMENTS

JP   S59-070384 A    4/1984
JP   2000-308643 A  11/2000
(Continued)

OTHER PUBLICATIONS

International Search Report dated Sep. 1, 2015 issued in PCT/JP2015/071511.
(Continued)

Primary Examiner — Vu Le
Assistant Examiner — Samah A Beg
(74) Attorney, Agent, or Firm — Scully, Scott, Murphy & Presser, P.C.

(57) ABSTRACT

An image processing apparatus processes a first image signal including pixel signals, the first image signal having a picture portion in which a subject is shown and having a blank portion surrounding the picture portion. The apparatus includes: a blank detection unit configured to set similar frames different in size from one another within a display area of a screen representing the first image signal, in a stepwise manner from an outer periphery, and to detect the
(Continued)

blank portion based on whether or not a part of the pixel signals belonging to a region outside each of the similar frames has the uniform color or brightness; a region-of-interest setting unit configured to set an initial region-of-interest corresponding to the picture portion in the first image signal, based on the blank portion; and a region-of-interest image generation unit configured to generate a region-of-interest image signal representing the initial region-of-interest.

7 Claims, 12 Drawing Sheets

(51) Int. Cl.

| | | |
|---|---|---|
| *G06T 7/11* | (2017.01) | |
| *A61B 1/00* | (2006.01) | |
| *A61B 6/00* | (2006.01) | |
| *A61B 8/08* | (2006.01) | |
| *G06T 11/60* | (2006.01) | |
| *G06T 7/12* | (2017.01) | |
| *A61B 6/12* | (2006.01) | |
| *A61B 8/12* | (2006.01) | |
| *A61B 8/00* | (2006.01) | |

(52) U.S. Cl.
CPC ............... *A61B 6/12* (2013.01); *A61B 6/463* (2013.01); *A61B 6/469* (2013.01); *A61B 6/5205* (2013.01); *A61B 6/5211* (2013.01); *A61B 6/5247* (2013.01); *A61B 8/12* (2013.01); *A61B 8/463* (2013.01); *A61B 8/469* (2013.01); *A61B 8/5207* (2013.01); *A61B 8/5215* (2013.01); *A61B 8/5261* (2013.01); *G06T 7/11* (2017.01); *G06T 7/12* (2017.01); *G06T 11/60* (2013.01); *G06T 2207/10024* (2013.01); *G06T 2207/10068* (2013.01); *G06T 2207/10116* (2013.01); *G06T 2207/10132* (2013.01); *G06T 2207/20132* (2013.01)

(56) References Cited

U.S. PATENT DOCUMENTS

| | | | | |
|---|---|---|---|---|
| 5,548,664 A * | 8/1996 | Knowlton | ........... | G06F 3/04817 358/464 |
| 5,889,881 A * | 3/1999 | MacAulay | ......... | G01N 15/1475 382/133 |
| 5,978,519 A * | 11/1999 | Bollman | ................... | G06T 7/70 382/270 |
| 5,995,661 A * | 11/1999 | Amidei | ..................... | G06T 7/12 358/462 |
| 6,009,195 A * | 12/1999 | Nakata | ................. | G06K 9/2018 358/452 |
| 6,545,743 B1 * | 4/2003 | Luo | ........................... | G06T 7/73 355/18 |
| 6,891,961 B2 * | 5/2005 | Eger | ....................... | A22B 5/007 382/110 |
| 7,171,058 B2 * | 1/2007 | Luo | ..................... | H04N 1/3875 358/453 |
| 7,492,388 B2 * | 2/2009 | Odlivak | ................. | G06Q 10/10 348/65 |
| 8,009,921 B2 * | 8/2011 | Csurka | ............... | G06K 9/00664 382/228 |
| 8,050,868 B2 * | 11/2011 | Rosania | ............. | G06K 9/00127 382/132 |
| 8,107,678 B2 * | 1/2012 | Feris | .................. | G06K 9/00771 382/103 |
| 8,208,715 B2 * | 6/2012 | Lau | .................... | G06K 9/00637 345/419 |
| 8,284,249 B2 * | 10/2012 | Feris | ..................... | G06T 7/2053 348/143 |
| 8,401,339 B1 * | 3/2013 | Anderson | ................ | G06K 9/36 382/298 |
| 8,471,898 B2 * | 6/2013 | Neuman | .............. | H04N 13/261 348/51 |
| 9,013,489 B2 * | 4/2015 | Evertt | ..................... | G06T 19/20 345/418 |
| 9,025,836 B2 * | 5/2015 | Ptucha | .................... | G06T 11/00 382/118 |
| 9,196,080 B2 * | 11/2015 | Neuman | ............... | H04N 13/261 |
| 9,342,881 B1 * | 5/2016 | Peleg | .................... | G06T 7/0012 |
| 9,864,925 B2 * | 1/2018 | Stieglitz | ............... | G06K 9/4671 |
| 9,881,207 B1 * | 1/2018 | Nguyen | ............. | G06K 9/00369 |
| 2006/0098889 A1 * | 5/2006 | Luo | ........................ | G06T 11/001 382/254 |
| 2006/0242669 A1 * | 10/2006 | Wogsberg | ................ | H04N 7/01 725/74 |
| 2006/0269275 A1 * | 11/2006 | Krause | ................. | G11B 27/034 396/310 |
| 2007/0081173 A1 * | 4/2007 | Yanada | .............. | H04N 5/23212 358/1.6 |
| 2007/0165119 A1 * | 7/2007 | Ikeda | ..................... | H04N 5/3572 348/246 |
| 2007/0229664 A1 * | 10/2007 | Nagaoka | .................. | H04N 5/20 348/173 |
| 2008/0019574 A1 * | 1/2008 | Scalise | ............... | G06K 9/00228 382/118 |
| 2008/0075388 A1 * | 3/2008 | Nishijima | .......... | G06K 9/00228 382/282 |
| 2009/0116713 A1 * | 5/2009 | Yan | ...................... | G06K 9/4619 382/128 |
| 2009/0149706 A1 | 6/2009 | Yamazaki et al. | | |
| 2009/0274393 A1 * | 11/2009 | Patel | .................... | H04N 1/3873 382/298 |
| 2009/0284806 A1 * | 11/2009 | Takata | ............... | H04N 1/00355 358/453 |
| 2009/0310861 A1 * | 12/2009 | Lang | ..................... | G06F 17/3025 382/173 |
| 2010/0157105 A1 * | 6/2010 | Yokohata | ................ | G02B 7/102 348/240.3 |
| 2010/0157107 A1 * | 6/2010 | Iijima | .................... | H04N 5/232 348/240.99 |
| 2010/0220238 A1 * | 9/2010 | Honda | .................... | H04N 9/646 348/663 |
| 2011/0085734 A1 * | 4/2011 | Berg | ................... | G06F 17/30802 382/195 |
| 2011/0157428 A1 * | 6/2011 | Kamiya | ...................... | G06T 7/85 348/240.2 |
| 2011/0164111 A1 * | 7/2011 | Karaoguz | ................. | G06F 3/14 348/E13.002 |
| 2011/0216937 A1 * | 9/2011 | Radhakrishnan | ........................ | G06F 17/30799 382/100 |
| 2013/0259365 A1 * | 10/2013 | Suzuki | .................. | G06K 9/4652 382/164 |
| 2013/0279563 A1 * | 10/2013 | Li | ........................ | H04N 19/115 375/240.02 |
| 2013/0321833 A1 * | 12/2013 | Yabuuchi | ................ | H04N 1/38 358/1.13 |
| 2014/0029787 A1 | 1/2014 | Koyama | | |
| 2014/0049566 A1 * | 2/2014 | Sudou | ..................... | G09G 5/38 345/681 |
| 2014/0172231 A1 * | 6/2014 | Terada | .................... | G06F 3/005 701/36 |
| 2014/0375781 A1 * | 12/2014 | Ono | .................... | G02B 23/2484 348/61 |
| 2015/0054853 A1 * | 2/2015 | Georgiev | ................. | G06T 3/40 345/660 |
| 2015/0135137 A1 * | 5/2015 | Miwa | ..................... | G06T 11/60 715/808 |
| 2015/0301771 A1 * | 10/2015 | Bae | ........................ | G06F 17/243 358/1.6 |
| 2017/0294038 A1 * | 10/2017 | Moriya | ..................... | G06T 3/40 |
| 2018/0129903 A1 * | 5/2018 | Stieglitz | ............... | G06K 9/4671 |

(56) References Cited

U.S. PATENT DOCUMENTS

FOREIGN PATENT DOCUMENTS

| | | |
|---|---|---|
| JP | 2004-343155 A | 12/2004 |
| JP | 2008-043604 A | 2/2008 |
| WO | WO 2012/140985 A1 | 10/2012 |

OTHER PUBLICATIONS

Japanese Office Action dated May 20, 2016 issued in Japanese Patent Application No. 2016-509227.

* cited by examiner

IMAGE PROCESSING APPARATUS FOR GENERATING COMBINED IMAGE SIGNAL OF REGION-OF-INTEREST IMAGE SIGNAL AND SECOND IMAGE SIGNAL, THE REGION-OF-INTEREST IMAGE SIGNAL BEING GENERATED BASED ON BLANK PORTION AND INITIAL REGION-OF-INTEREST OF FIRST IMAGE SIGNAL

CROSS REFERENCES TO RELATED APPLICATIONS

This application is a continuation of PCT international application Ser. No. PCT/JP2015/071511, filed on Jul. 29, 2015 which designates the United States, incorporated herein by reference, and which claims the benefit of priority from Japanese Patent Application No. 2014-154914, filed on Jul. 30, 2014, incorporated herein by reference.

BACKGROUND

1. Technical Field

The disclosure relates to an image processing apparatus for processing an image signal having a picture portion in which a subject is shown and having a blank portion.

2. Related Art

In a medical field, there are cases where an endoscope for imaging inside a subject is combined with a diagnosis apparatus to perform X-ray diagnosis or ultrasound diagnosis, and then, diagnosis is performed by using an X-ray image or an ultrasound image, together with an endoscopic image. Recently, in order to reduce the burden on an operator including a doctor, who performs diagnosis while comparing a monitor displaying an X-ray image or an ultrasound image, with an endoscopic image monitor, a method is proposed (e.g. refer to JP 2000-308643 A) whereby an X-ray image or an ultrasound image is input into an endoscope processor and using two screens, namely, an endoscopic image screen and a screen that displays the X-ray image or the ultrasound image, as a parent-child screen, simultaneous display of images on one monitor is performed.

SUMMARY

In some embodiments, provided is an image processing apparatus for processing a first image signal including a plurality of pixel signals, the first image signal having a picture portion in which a subject is shown and having a blank portion surrounding the picture portion. The image processing apparatus includes: a blank detection unit configured to detect, as the blank portion, a portion having uniform color or brightness in the first image signal, based on the plurality of pixel signals; a region-of-interest setting unit configured to set an initial region-of-interest corresponding to the picture portion in the first image signal, based on the blank portion detected by the blank detection unit; and a region-of-interest image generation unit configured to generate a region-of-interest image signal representing the initial region-of-interest set by the region-of-interest setting unit. The blank detection unit is configured to: set a plurality of similar frames different in size from one another within a display area of a screen representing the first image signal, in a stepwise manner from an outer periphery; and detect the blank portion based on whether or not a part of the plurality of pixel signals belonging to a region outside each of the plurality of similar frames has the uniform color or brightness.

The above and other features, advantages and technical and industrial significance of this invention will be better understood by reading the following detailed description of presently preferred embodiments of the invention, when considered in connection with the accompanying drawings.

DETAILED DESCRIPTION

Hereinafter, a processing apparatus that displays an endoscopic image and an X-ray image on a display device will be described according to embodiments of the present invention (hereinafter, referred to as "embodiment(s)"). Note that the present invention is not intended to be limited by these embodiments. The same reference signs are used to designate the same elements throughout the drawings.

First Embodiment

Figure 1:
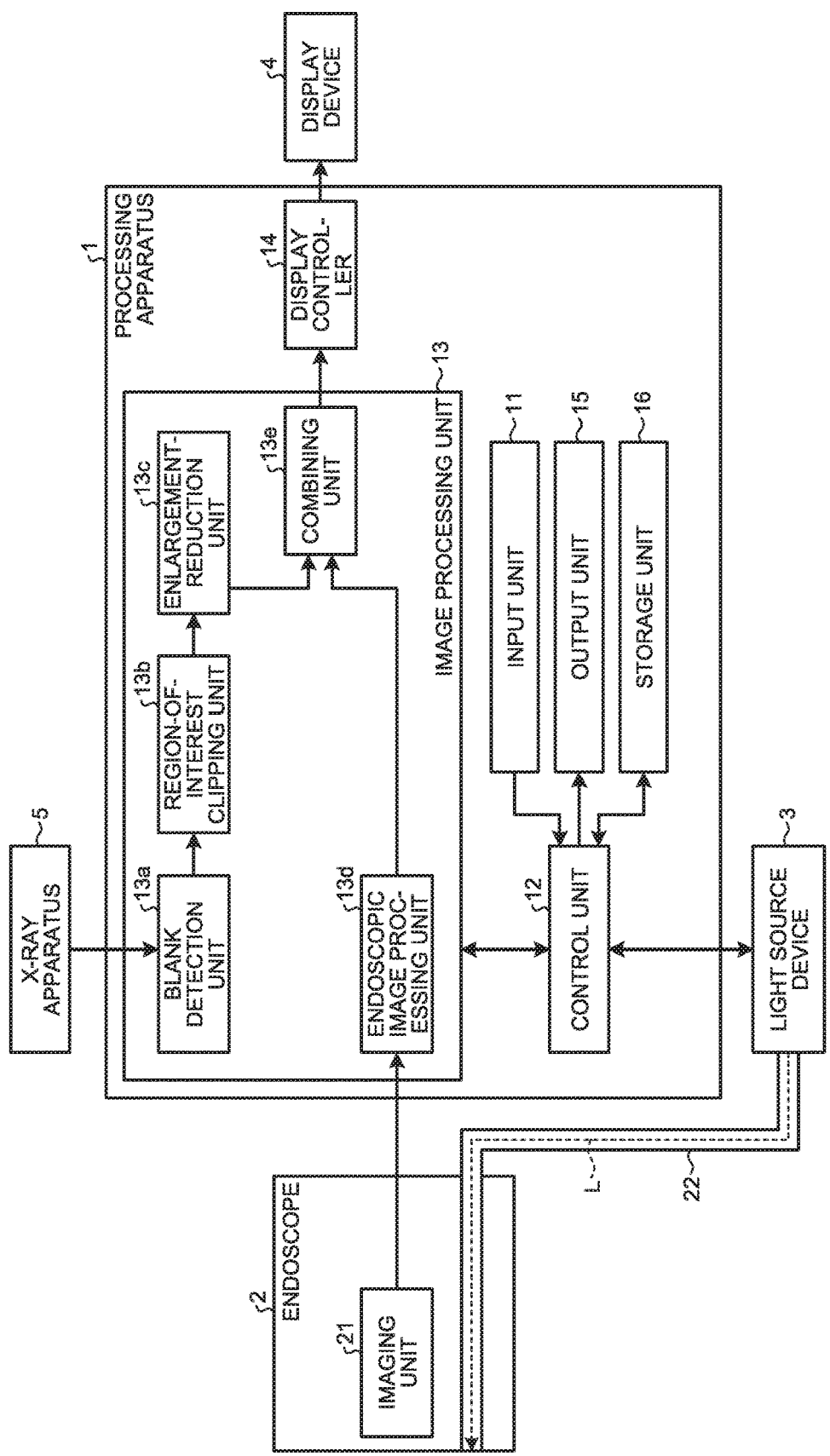
FIG. 1 is a block diagram schematically illustrating a configuration of a processing apparatus according to a first embodiment of the present invention.

FIG. 1 is a block diagram schematically illustrating a configuration of a processing apparatus according to a first embodiment of the present invention.

As illustrated in FIG. 1, a processing apparatus 1 according to the first embodiment is connected to an endoscope 2 (scope) including an imaging unit 21 configured to be introduced into a subject, image internal portions of the subject, and generate an endoscopic image signal, a light source device 3 configured to generate illumination light L and supplies the light to a distal end of the endoscope 2 via a light guide cable 22, a display device 4 including a display, or the like, using liquid crystal or organic electro luminescence (EL), and an X-ray apparatus 5 configured to generate an X-ray image signal. The processing apparatus 1 performs predetermined image processing on an endoscopic image signal input from the endoscope 2, performs predetermined image processing also on an X-ray image signal input from the X-ray apparatus 5, and displays, on the display device 4, an image corresponding to a combined image signal generated by arranging and combining the endoscopic image signal and the X-ray image signal after image processing. The processing apparatus 1 displays, on a display screen of the display device 4, the combined image signal that represents two screens, namely, a screen that displays an image that corresponds to the X-ray image signal, and a screen that displays the endoscopic image signal, as a parent-child screen. The processing apparatus 1 also controls operation of each of the endoscope 2, the light source device 3, and the display device 4.

The processing apparatus 1 includes an input unit 11, a control unit 12, an image processing unit 13, a display controller 14, an output unit 15, and a storage unit 16.

The input unit 11 includes an operation device such as a mouse, a keyboard, and a touch panel, and receives input of various types of instruction information. Specifically, the input unit 11 receives input of various types of instruction information including information on the subject under examination with the endoscope 2 and the X-ray apparatus 5 (for example, ID, date of birth, and name), identification information of the endoscope 2 (for example, ID and examination items), identification information of the X-ray apparatus 5, and details of examination.

The control unit 12 includes a CPU. The control unit 12 controls processing operation of components of the processing apparatus 1. The control unit 12 controls operation of the processing apparatus 1 by performing transfer, or the like, of instruction information or data toward individual components of the processing apparatus 1. The control unit 12 is connected, via individual cables, to the constituent sites of the imaging unit 21 and the light source device 3, and to the display device 4. The control unit 12 controls operation of the imaging unit 21, the light source device 3, and the display device 4, as well.

Under control of the control unit 12, the image processing unit 13 performs predetermined signal processing on the endoscopic image signal generated by the imaging unit 21 and on the X-ray image signal input from the X-ray apparatus 5. The image processing unit 13 includes a blank detection unit 13a, a region-of-interest clipping unit 13b (region-of-interest setting unit and clipping unit), an enlargement-reduction unit 13c, an endoscopic image processing unit 13d, and a combining unit 13e. The X-ray image signal is an image signal having a picture portion in which a subject is shown to draw the operator's attention, and having a blank portion surrounding the picture portion. The blank portion is a uniform region having uniform brightness or uniform color.

The blank detection unit 13a detects a blank portion of an X-ray image signal by detecting a change in brightness or color, in the X-ray image signal.

Based on the blank portion of the X-ray image signal detected by the blank detection unit 13a, the region-of-interest clipping unit 13b set an initial region-of-interest that corresponds to the picture portion of the X-ray image signal, and together with this, clips the set initial region-of-interest from the X-ray image signal.

The enlargement-reduction unit 13c enlarges or reduces the initial region-of-interest clipped from the X-ray image signal by the region-of-interest clipping unit 13b depending on the size of the X-ray image display screen of the display device 4 for displaying the X-ray image signal, thereby to generate a region-of-interest image signal representing the initial region-of-interest.

The endoscopic image processing unit 13d performs, on the endoscopic image signal input from the endoscope 2, various types of image processing including optical black subtraction processing, gain adjustment processing, image signal synchronization processing, gamma correction processing, white balance (WB) adjustment processing, color matrix computing processing, color reproduction processing, and edge emphasis processing.

The combining unit 13e arranges and combines the region-of-interest image signal generated by the enlargement-reduction unit 13c and the endoscopic image signal processed by the endoscopic image processing unit 13d, thereby to generate a combined image signal, and outputs the combined image signal.

The display controller 14 generates a display image signal to be displayed on the display device 4 from the combined image signal output from the combining unit 13e, and converts the generated display image signal from a digital signal into an analog signal. Thereafter, the display controller 14 changes the format of the analog image signal to a format such as a high-vision system and outputs the signal to the display device 4. Note that functions of the display controller 14 might be partially provided on the display device 4 in some cases.

The output unit 15 includes a speaker and a printer, and outputs information on display processing of an endoscopic image signal and an X-ray image signal, according to the control of the control unit 12.

The storage unit 16 includes a volatile memory and a non-volatile memory, and stores various programs for operating the processing apparatus 1, the endoscope 2, and the light source device 3. The storage unit 16 temporarily stores information being processed by the processing apparatus 1. The storage unit 16 can also be formed with a memory card, or the like, attached from outside of the processing apparatus 1.

Figure 2:
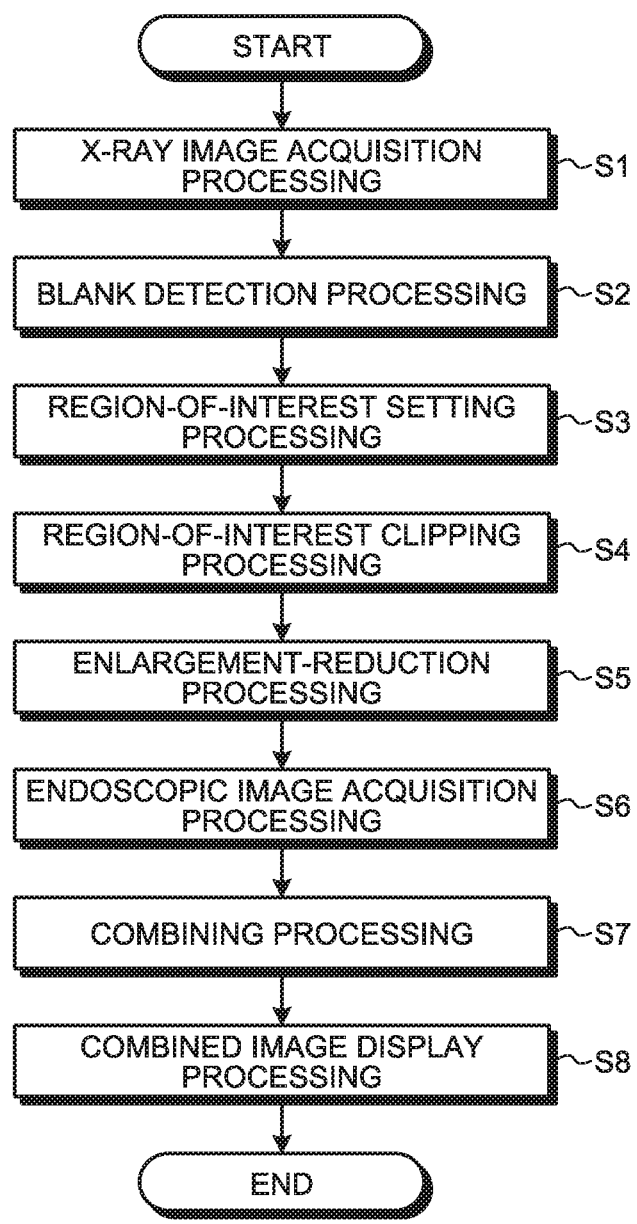
FIG. 2 is a flowchart illustrating a processing procedure for displaying an image corresponding to an X-ray image signal and to an endoscopic image signal, on a display device by the processing apparatus illustrated in FIG. 1.

FIG. 2 is a flowchart illustrating a processing procedure for displaying an image corresponding to an X-ray image signal and to an endoscopic image signal, on the display device 4 by the processing apparatus 1. As illustrated in FIG. 2, initially on the processing apparatus 1, the image processing unit 13 performs X-ray image acquisition processing for obtaining an X-ray image signal input from the X-ray apparatus 5 (step S1).

Figure 3:
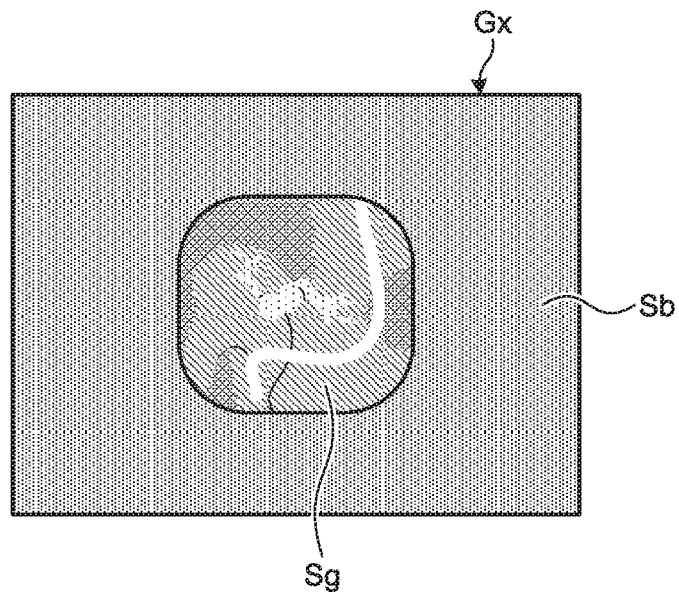
FIG. 3 is diagram illustrating an exemplary X-ray image signal input into the processing apparatus illustrated in FIG. 1.

FIG. 3 is diagram illustrating an exemplary X-ray image signal input into the processing apparatus 1. As illustrated in FIG. 3, an X-ray image signal Gx input from the X-ray apparatus 5 includes a picture portion Sg in which a subject is shown, and a blank portion Sb, which is a uniform region having uniform brightness or uniform color, surrounding the picture portion Sg.

On the image processing unit 13, the blank detection unit 13a performs blank detection processing for detecting a blank portion of the X-ray image signal Gx (step S2).

Figure 4:
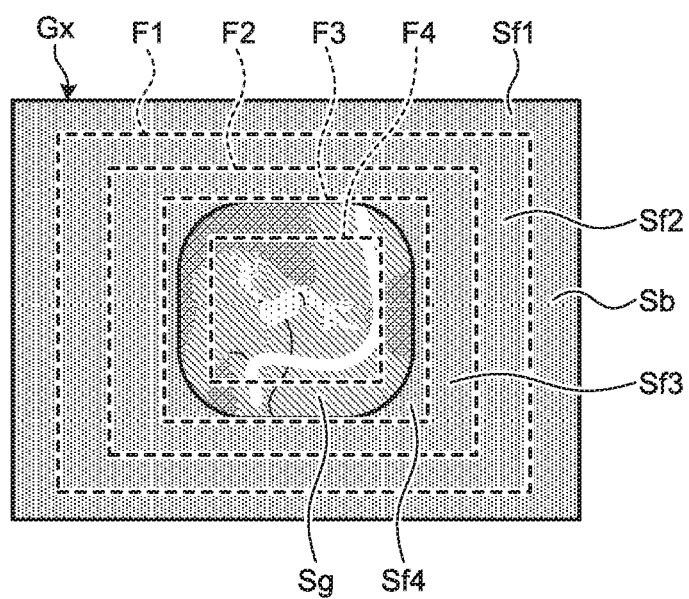
FIG. 4 is a diagram for illustrating blank detection processing illustrated in FIG. 2.

For example, the blank detection unit 13a detects a blank portion by gradually detecting a color change of a predetermined region beginning with an outer peripheral portion of the X-ray image signal Gx. FIG. 4 is a diagram for illustrating blank detection processing performed by the blank detection unit 13a. As illustrated in FIG. 4, a plurality of frames F1 to F4 is set. Each of these frames is similar in shape to the display area of the screen that displays the X-ray image signal Gx. The blank detection unit 13a detects, for each of regions Sf1 to Sf4 located outside the frames F1 to F4, whether the color or brightness of the regions Sf1 to Sf4 is uniform. In a case where the blank detection unit 13a determines that the color or brightness is uniform in the determination-target regions Sf1 to Sf4 on the basis on the image signal of each of the regions Sf1 to Sf4, the blank detection unit 13a detects that the determination-target regions Sf1 to Sf4 as blank portions. In contrast, in a case where the blank detection unit 13a determines that the color or brightness is non-uniform in the determination-target regions Sf1 to Sf4, the blank detection unit 13a determines that the determination-target regions Sf1 to Sf4 include a picture portion, determines a portion outside the frame located just outside the frames F1 to F4 that correspond to the regions Sf1 to Sf4, as a blank portion, and finishes the blank detection processing. In the example illustrated in FIG. 4, the color or brightness is uniform in the region Sf1 outside the frame F1, the region Sf2 outside the frame F2 and inside the frame F1, and the region Sf3 outside the frame F3 and inside the frame F2. In contrast, the color or brightness is non-uniform in the region Sf4 outside the frame F4 and inside the frame F3. Accordingly, the blank detection unit 13a determines that the region Sf4 is not a blank portion but a region corresponding to the picture portion, and detects that the region outside the frame F3 as a blank portion.

Moreover, it is also allowable to configure such that the blank detection unit 13a scans horizontal lines sequentially from the top toward the X-ray image signal Gx, obtains for each of pixels, brightness data and color data in the horizontal direction, and detects a blank portion based on the presence or absence of a change in the brightness data and the color data. For example, in a case where horizontal lines 1 to 50 of the X-ray image signal Gx have no change in the brightness or color in any of the pixels, that is being uniform, the blank detection unit 13a determines that the regions that correspond to the horizontal lines 1 to 50 are blank portions. In a case where a horizontal line 51 has no change in one of brightness and color in pixels 1 to 30, and pixels 251 to 300, that is being uniform, and has a change in brightness or color in pixels 31 to 250, the blank detection unit 13a determines that regions that correspond to the pixels 31 to 250 on the horizontal line 51 are picture portions. In this manner, the blank detection unit 13a repeats brightness and color scanning for each of the pixels per horizontal line, and detects a portion having uniform brightness or uniform color, as a blank portion.

Subsequently, on the image processing unit 13, the region-of-interest clipping unit 13b performs region-of-interest setting processing for setting an initial region-of-interest corresponding to the picture portion of the X-ray image signal Gx (step S3) based on the blank portion detected by the blank detection unit 13a, and performs region-of-interest clipping processing for clipping the initial region-of-interest set in the region-of-interest setting processing, from the X-ray image signal Gx (step S4). Subsequently, the enlargement-reduction unit 13c performs enlargement-reduction processing for enlarging or reducing the initial region-of-interest clipped from the X-ray image signal Gx in the region-of-interest clipping processing performed by the region-of-interest clipping unit 13b, corresponding to the size of a display for the X-ray image signal Gx (step S5), and generates the X-ray image signal after enlargement or reduction, as a region-of-interest image signal representing an initial region-of-interest. The enlargement-reduction unit 13c outputs the generated region-of-interest image signal to the combining unit 13e.

Figure 5:
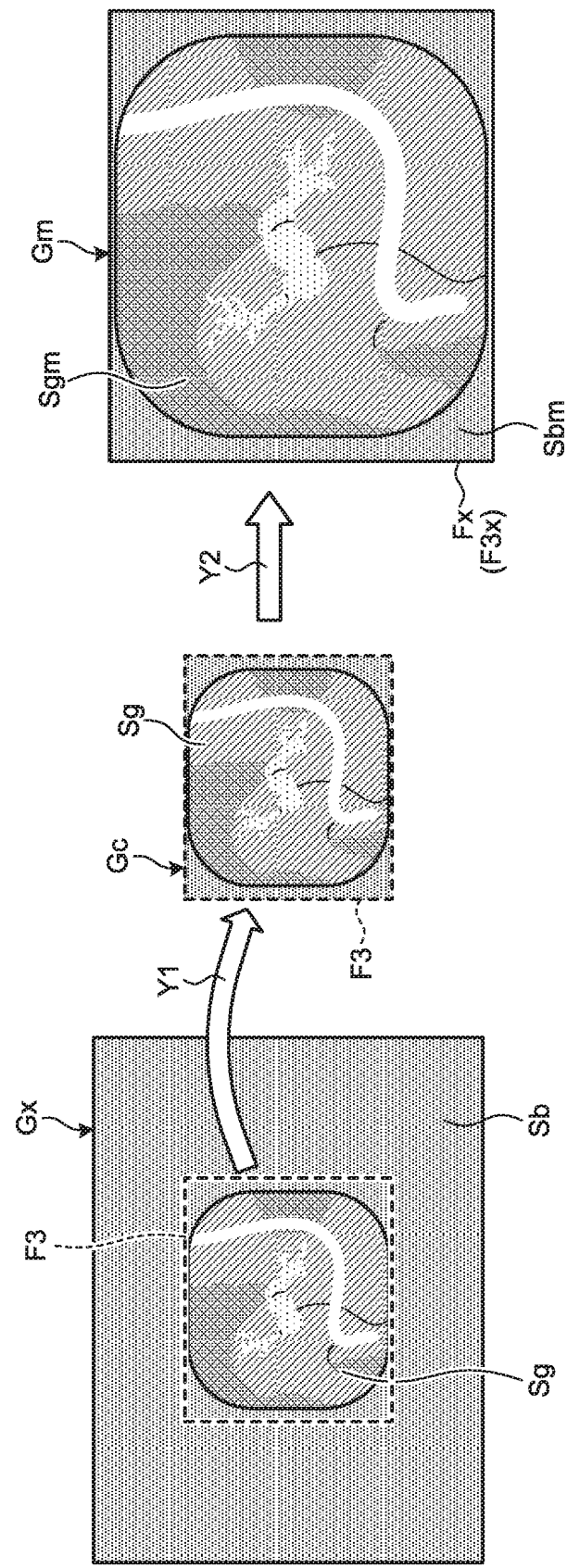
FIG. 5 is a diagram illustrating region-of-interest setting processing, region-of-interest clipping processing, and enlargement-reduction processing illustrated in FIG. 2.

FIG. 5 is a diagram illustrating steps S3 to S5 illustrated in FIG. 2. As illustrated in FIG. 4, in a case where the blank detection unit 13a detects that blank portion Sb of the X-ray image signal Gx is a region outside the frame F3, the region-of-interest clipping unit 13b sets, as illustrated in a left-hand side of FIG. 5, the region surrounded by the frame F3 as an initial region-of-interest including the picture portion Sg. Subsequently, as illustrated by arrow Y1, the region-of-interest clipping unit 13b clips the set region from the X-ray image signal Gx, together with the frame F3. Subsequently, the enlargement-reduction unit 13c enlarges an image signal Gc (refer to a center of FIG. 5) in the region clipped by the region-of-interest clipping unit 13b, corresponding to the size of the display area of the screen (parent screen Fx) on which the X-ray image signal Gx is displayed, as illustrated by arrow Y2. As a result, as illustrated in a right-hand side of FIG. 5, the ratio of a blank portion Sbm to the entire image is decreased to generate an X-ray image signal Gm so that a picture portion Sgm is larger than the original size. Note that the frame F3 is also enlarged into a frame F3x having the size same as the size of the parent screen Fx. The enlargement-reduction unit 13c outputs the X-ray image signal Gm to the combining unit 13e, as a region-of-interest image signal representing the initial region-of-interest.

The image processing unit 13 performs endoscopic image acquisition processing (step S6) for obtaining an endoscopic image signal imaged by the endoscope 2 corresponding to the imaging timing of the X-ray image signal Gx obtained in step S1, causes the endoscopic image processing unit 13d to perform predetermined image processing on the obtained endoscopic image signal, and thereafter outputs the processed signal to the combining unit 13e. Note that steps S1 to S5 and step S6 may be performed in any order, even may be performed in parallel.

The combining unit 13e performs combining processing for arranging and combining the region-of-interest image signal generated by the enlargement-reduction unit 13c and the endoscopic image signal processed by the endoscopic image processing unit 13d, thereby generating and outputting a combined image signal (step S7).

Figure 6:
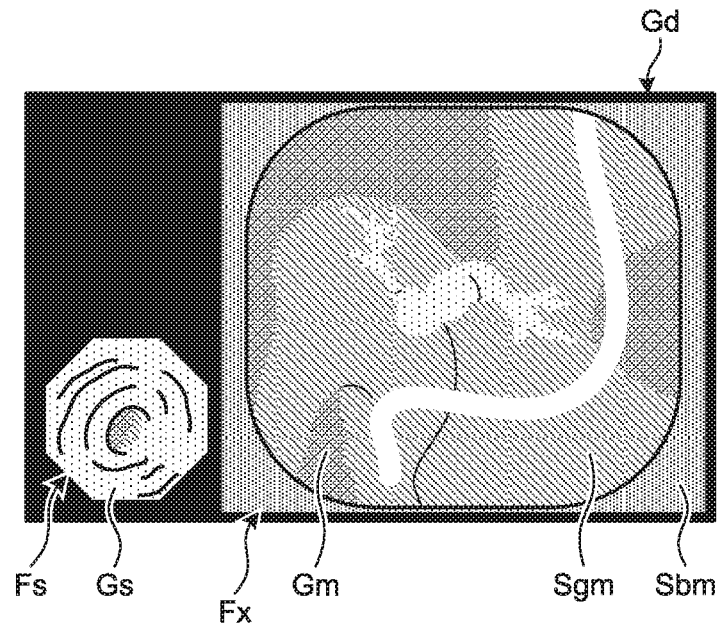
FIG. 6 is a diagram illustrating an exemplary combined image signal generated by a combining unit illustrated in FIG. 1.

FIG. 6 is a diagram illustrating an exemplary combined image signal generated by the combining unit 13e. As illustrated in FIG. 6, the combining unit 13e arranges the X-ray image signal Gm as a region-of-interest image signal output from the enlargement-reduction unit 13c, within a right-side parent screen Fx, generates a parent-child screen image Gd having the endoscopic image signal Gs output from the endoscopic image processing unit 13d being arranged within a left-side child screen Fs, and outputs the generated signal to the display controller 14. The display controller 14 performs combined image display processing (step S8) for converting the parent-child screen image Gd generated by the combining unit 13e into a display image signal and displaying the signal on the display device 4. One X-ray image signal Gm combined by the combining unit 13e represents the initial region-of-interest that corresponds to the picture portion Sgm displayed in a larger size compared with the originally input X-ray image signal Gx. Since the ratio of the blank portion Sbm to the entire image is small, the X-ray image having the picture portion Sgm displayed in a large size is displayed on the parent screen Fx. Although the examples of FIGS. 5 and 6 describe cases where the enlargement-reduction unit 13c enlarges the image signal Gc, it is, of course, not limited to enlargement. It is allowable to configure such that, in a case where the image signal Gc is larger than the parent screen Fx, the enlargement-reduction unit 13c reduces the image signal Gc in accordance with the size of the parent screen Fx to include the entire image signal Gc in the parent screen Fx so as to enable the operator to check the entire picture portion of the X-ray image.

Figure 7:
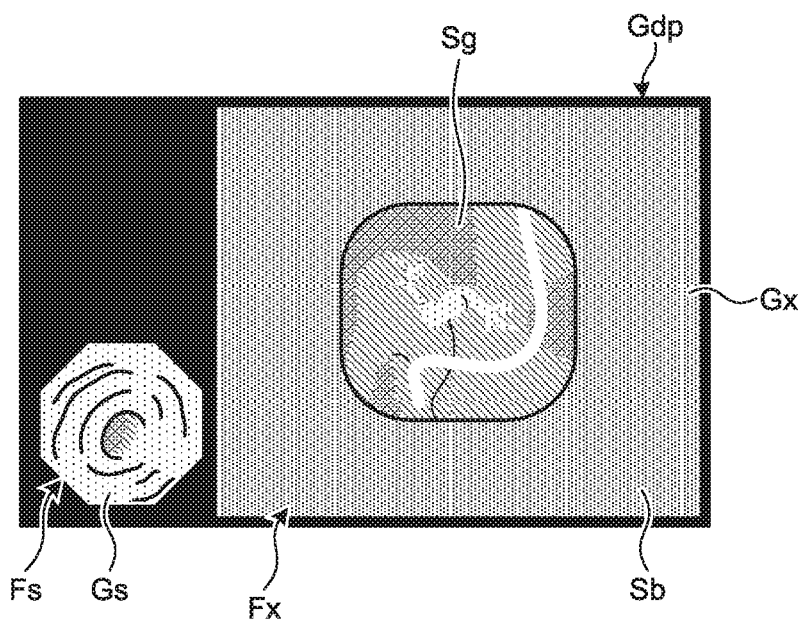
FIG. 7 is a diagram illustrating an exemplary combined image signal generated by a processing apparatus according to a conventional technique.

According to a conventional technique, the X-ray image signal Gx input from an external X-ray apparatus is aligned as it is, with the endoscopic image signal Gs. Therefore, as shown in the parent-child screen image Gdp of FIG. 7, the ratio of the picture portion Sg to the entire image is small, which makes it difficult for the operator to observe a lesion or the like.

In contrast, according to the first embodiment, the ratio of the region that corresponds to the picture portion Sgm to the entire image is greater when compared with the originally input X-ray image signal Gx on the X-ray image signal Gm combined by the combining unit 13e. Accordingly, the picture portion Sgm is displayed in a larger size on the parent screen Fx. Of course, since the enlargement-reduction unit 13c can also reduce the image signal Gc in accordance with the size of the parent screen Fx on the display device 4, automatic display is performed on the display device 4 so as to include the entire initial regions-of-interest within the parent screen Fx.

In this manner, in the first embodiment, an image appropriately representing the initial region-of-interest that corresponds to the picture portion that interests the operator is automatically displayed from the input X-ray image signal Gx. Therefore, according to the first embodiment, it is possible to significantly reduce the burden on the operator, in confirming the initial region-of-interest, and together with this, possible to appropriately assist observation of the entire picture portion by the operator, on the X-ray image.

Figure 8:
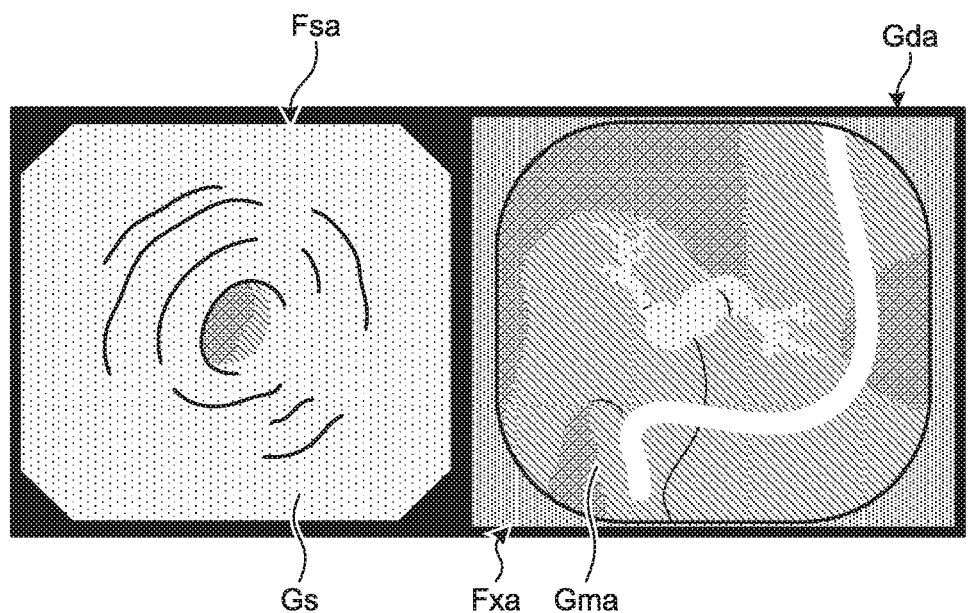
FIG. 8 is a diagram illustrating another exemplary combined image signal generated by a combining unit illustrated in FIG. 1.

Note that the combining unit 13e may not only generate the parent-child screen image Gd illustrated in FIG. 6 but also generate a parent-child screen image in which the X-ray image signal Gm is arranged within the child screen Fs of the parent-child screen, and the endoscopic image signal Gs is arranged within the parent screen Fx of the parent-child screen. Moreover, as illustrated in FIG. 8, the combining unit 13e may generate a screen image Gda in which the X-ray image signal Gma and the endoscopic image signal Gs are respectively arranged in screens Fsa and Fxa, having a substantially the same size.

Second Embodiment

Figure 9:
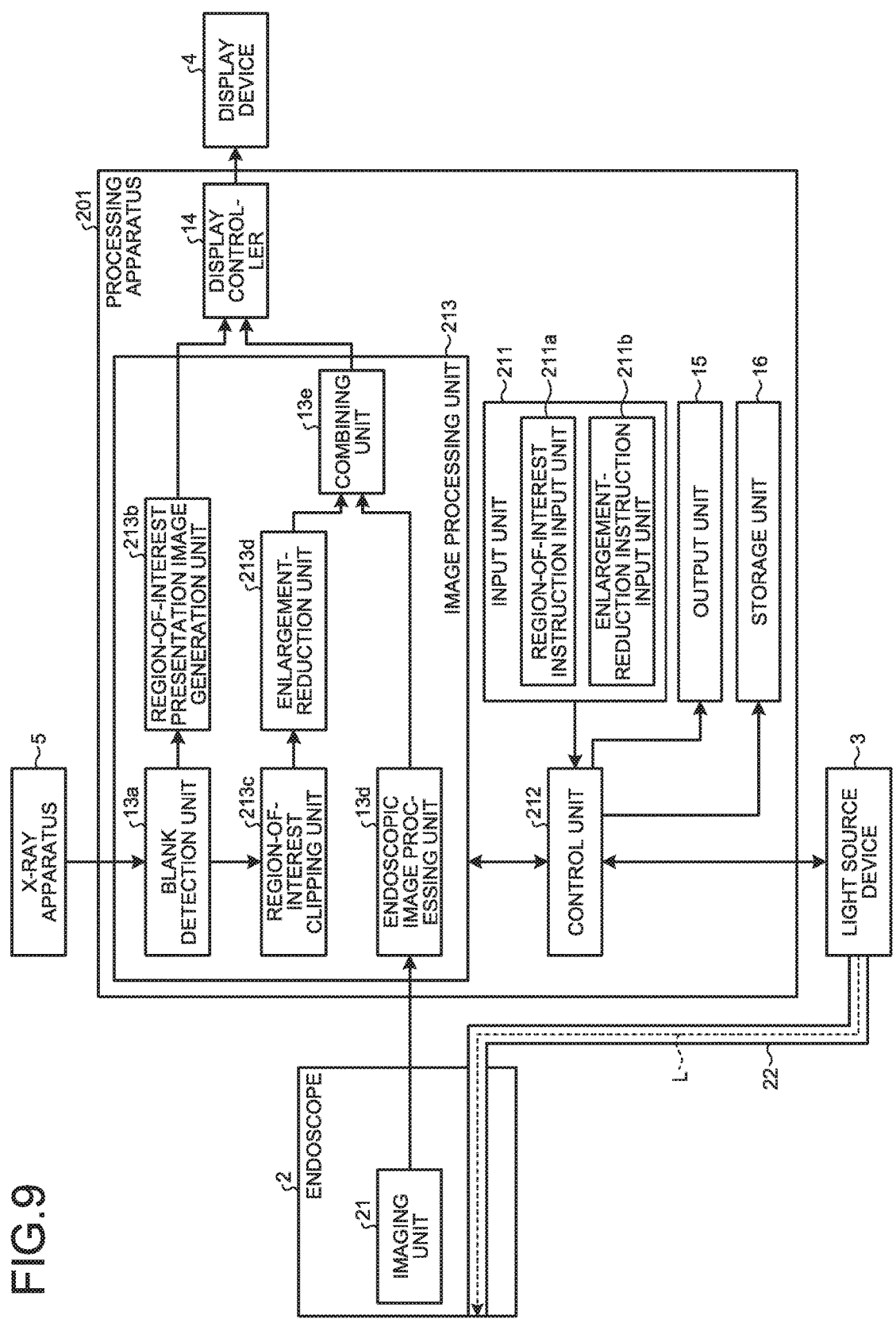
FIG. 9 is a block diagram schematically illustrating a configuration of a processing apparatus according to a second embodiment of the present invention.

Next, a second embodiment will be described. FIG. 9 is a block diagram schematically illustrating a configuration of a processing apparatus according to the second embodiment.

In comparison with the processing apparatus 1, a processing apparatus 201 according to the second embodiment, as illustrated in FIG. 9, includes an input unit 211, a control unit 212, and an image processing unit 213, in place of the input unit 11, the control unit 12, and the image processing unit 13, respectively. The control unit 212 has a function similar to the function of the control unit 12.

The input unit 211 has a function similar to the function of the input unit 11, and further includes a region-of-interest instruction input unit 211a, and an enlargement-reduction instruction input unit 211b. The region-of-interest instruction input unit 211a receives input of region-of-interest instruction information that instructs a region-of-interest for display, according to an instruction of the operator. The enlargement-reduction instruction input unit 211b receives input of enlargement-reduction instruction information that instructs enlargement or reduction of the region-of-interest for display, that is clipped by a region-of-interest clipping unit 213c to be described below, according to an instruction of the operator.

The image processing unit 213 includes the blank detection unit 13a, a region-of-interest presentation image generation unit 213b (region-of-interest image generation unit), the region-of-interest clipping unit 213c (clipping unit), an enlargement-reduction unit 213d, the endoscopic image processing unit 13d, and the combining unit 13e.

The region-of-interest presentation image generation unit 213b sets an initial region-of-interest that corresponds to the picture portion on the X-ray image signal Gx based on the blank portion detected by the blank detection unit 13a, and together with this, generates and outputs a region-of-interest presentation image signal (region-of-interest image signal) represented by superposing a frame surrounding the set initial region-of-interest onto the X-ray image signal Gx. The display controller 14 displays, on the display device 4, an image that corresponds to the region-of-interest presentation image signal output by the region-of-interest presentation image generation unit 213b. The operator can grasp the initial region-of-interest that corresponds to the picture portion by confirming the frame region on the image. The operator further operates an input device to change the frame size to a desired size and instructs a region surrounded by the frame after change as a region (region-of-interest for display) to be displayed on a display screen of the display device 4. The region-of-interest instruction input unit 211a receives the change in the frame size and inputs region-of-interest instruction information for designating the region surrounded by the frame after change as the region-of-interest for display, into the image processing unit 213 via the control unit 212.

Based on the region-of-interest instruction information input from the region-of-interest instruction input unit 211a, the region-of-interest clipping unit 213c clips a region-of-interest for display from the X-ray image signal Gx. The display controller 14 displays an image that corresponds to the region-of-interest for display clipped by the region-of-interest clipping unit 213c, on the display device 4. The operator instructs so as to enlarge or reduce the region-of-interest instructed by oneself, into a desired size by operating an input device. According to the operation by the operator, the enlargement-reduction instruction input unit 211b receives input of enlargement-reduction instruction information for instructing enlargement or reduction toward the region-of-interest for display, and inputs the enlargement-reduction instruction information into the image processing unit 213 via the control unit 212. Based on the enlargement-reduction instruction information input from the enlargement-reduction instruction input unit 211b, the enlargement-reduction unit 213d generates an X-ray image signal produced by enlarging or reducing the region-of-interest for display, clipped by the region-of-interest clipping unit 213c, and outputs the generated signal to the combining unit 13e. The combining unit 13e arranges and combines the X-ray image signal generated by the enlargement-reduction unit 213d and the endoscopic image signal Gs processed by the endoscopic image processing unit 13d, thereby to generate and output a combined image signal.

Figure 10:
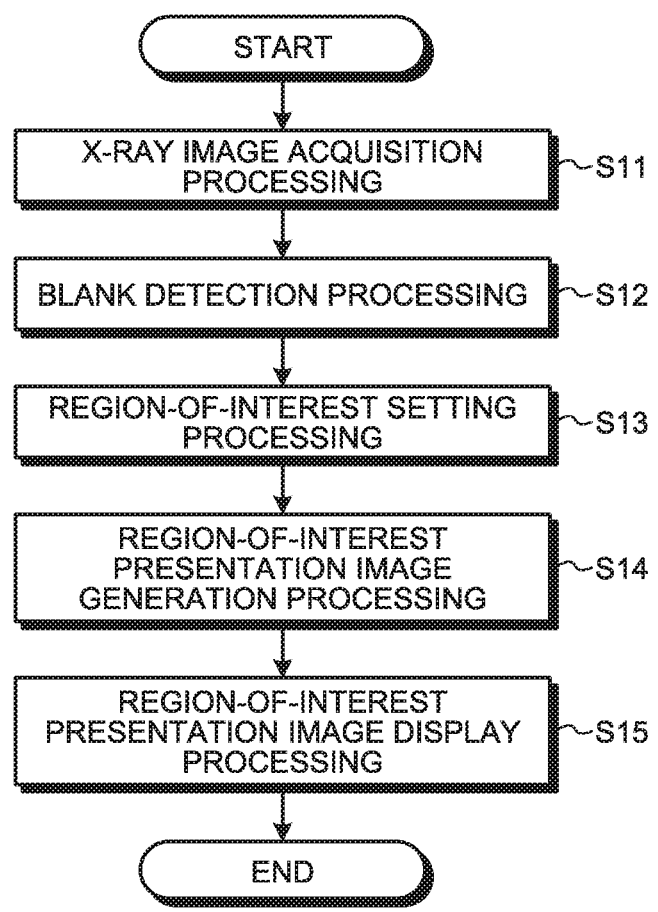
FIG. 10 is a flowchart illustrating a processing procedure for displaying a region-of-interest presentation image representing an initial region-of-interest, on a display device, by the processing apparatus illustrated in FIG. 9.

FIG. 10 is a flowchart illustrating a processing procedure for displaying a region-of-interest presentation image representing an initial region-of-interest, on the display device 4 by the processing apparatus 201. Steps S11 and S12 illustrated in FIG. 10 correspond to steps S1 and S2 illustrated in FIG. 2, respectively.

Based on the blank portion detected in the blank detection processing, the region-of-interest presentation image generation unit 213b performs region-of-interest setting processing for setting an initial region-of-interest corresponding to the picture portion in the X-ray image signal Gx (step S13). The region-of-interest presentation image generation unit 213b performs region-of-interest presentation image generation processing for superposing the frame surrounding the initial region-of-interest set in the region-of-interest setting processing, onto the X-ray image signal Gx, thereby generating a region-of-interest presentation image signal (step S14).

Figure 11:
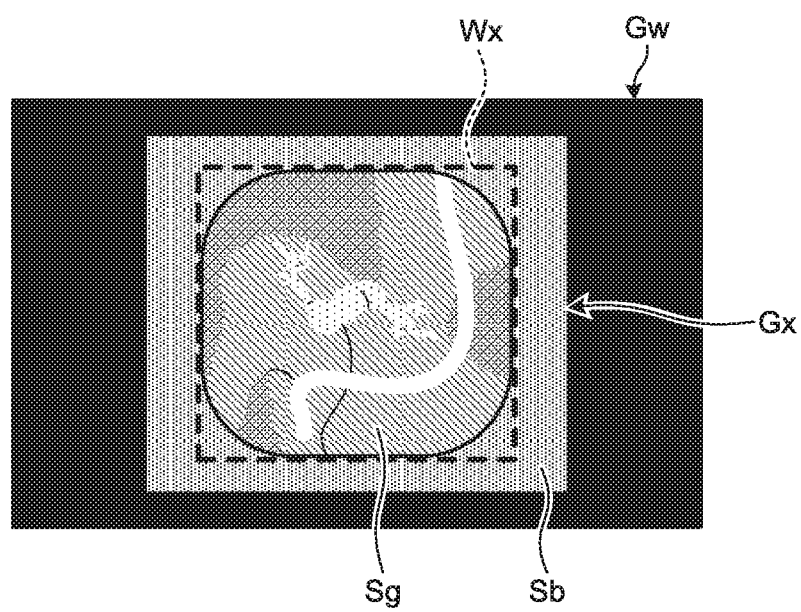
FIG. 11 is a diagram illustrating an exemplary image that corresponds to a region-of-interest image signal.

FIG. 11 is a diagram illustrating an exemplary image that corresponds to a region-of-interest presentation image signal. As illustrated in FIG. 11, based on the result of detection by the blank detection unit 13a, the region-of-interest presentation image generation unit 213b sets a region surrounded by a frame Wx as an initial region-of-interest, and generates an image signal Gw represented by superposing the frame Wx onto the X-ray image signal Gx, as a region-of-interest presentation image signal. The display controller 14 performs region-of-interest presentation image display processing for displaying, on the display device 4, an image that corresponds to the region-of-interest presentation image signal generated by the region-of-interest presentation image generation unit 213b (step S15). As a result, the image that corresponds to the image signal Gw illustrated in FIG. 11, is displayed on a display screen of the display device 4.

Figure 12:
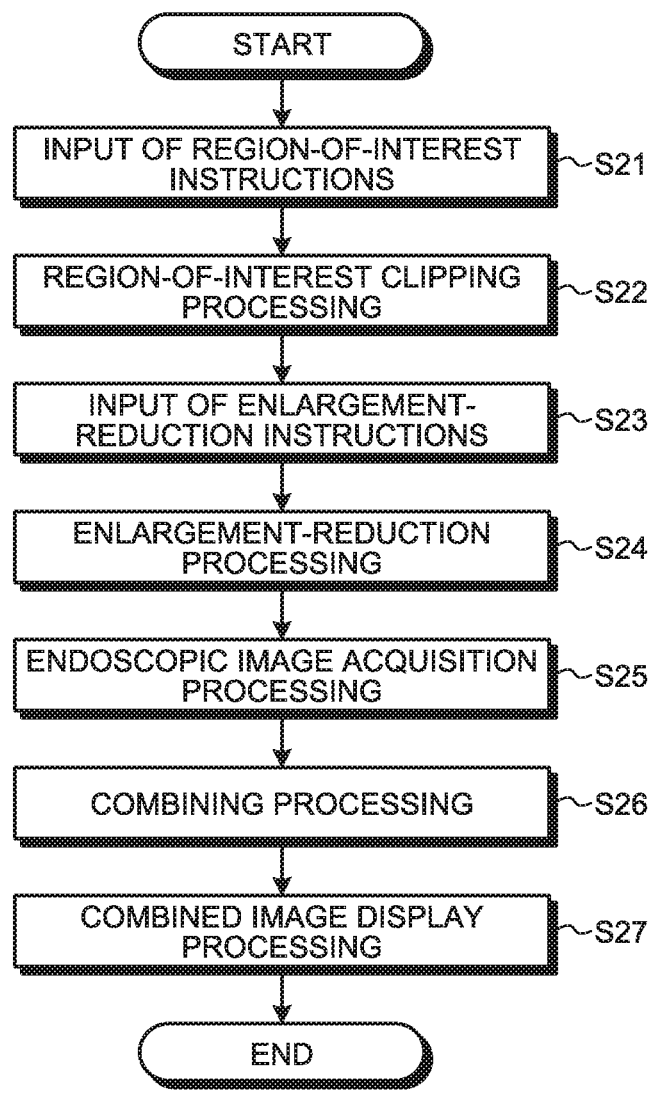
FIG. 12 is a flowchart illustrating a processing procedure for displaying a combined screen image generated by combining an X-ray image signal with an endoscopic image signal, on a display device, by the processing apparatus illustrated in FIG. 9.

FIG. 12 is a flowchart illustrating a processing procedure for displaying a combined image signal generated by combining the X-ray image signal Gx with the endoscopic image signal Gs, on the display device 4 by the processing apparatus 201. In step S15 in the above-described FIG. 10, the image corresponding to the image signal Gw, namely, the region-of-interest presentation image signal, is displayed on a display screen of the display device 4. Accordingly, the operator changes the size of the frame Wx surrounding the initial region-of-interest by operating the input device, and instructs the region surrounded by the frame after change, as a region-of-interest for display. As a result, region-of-interest instruction information for designating the region-of-interest for display, is input from the region-of-interest instruction input unit 211a into the image processing unit 213 (step S21) via the control unit 212.

Figure 13A:
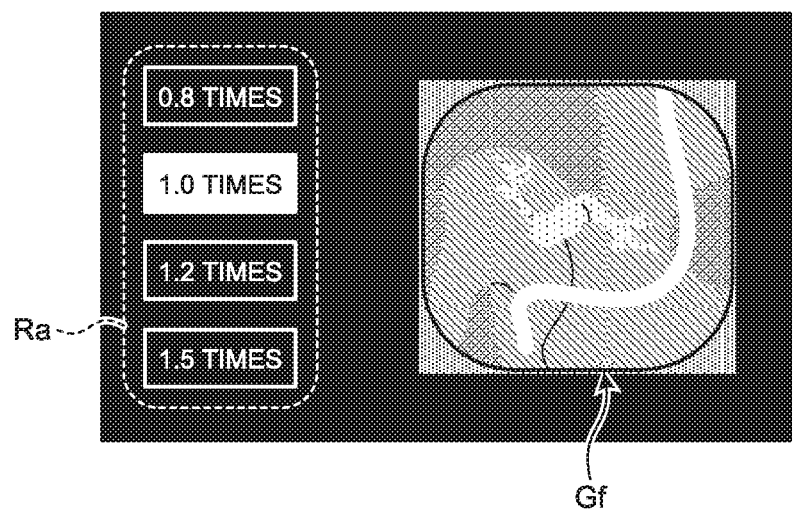
FIGS. 13A and 13B are diagrams illustrating region-of-interest clipping processing, input of enlargement-reduction instructions, and enlargement-reduction processing illustrated in FIG. 12.

Subsequently, based on region-of-interest instruction information, the region-of-interest clipping unit 213c performs region-of-interest clipping processing for clipping the region-of-interest for display, from the X-ray image signal Gx (step S22). In this case, as illustrated in FIG. 13A, the display controller 14 displays an image signal Gf that corresponds to the region-of-interest for display clipped by the region-of-interest clipping unit 213c, on a right-side region of the display screen, and together with this, displays an icon image enabling selection of various enlargement-reduction magnifications, on a left-side region Ra of the display screen. The operator selects a desired magnification toward the image signal Gf by operating the input device.

Figure 13B:
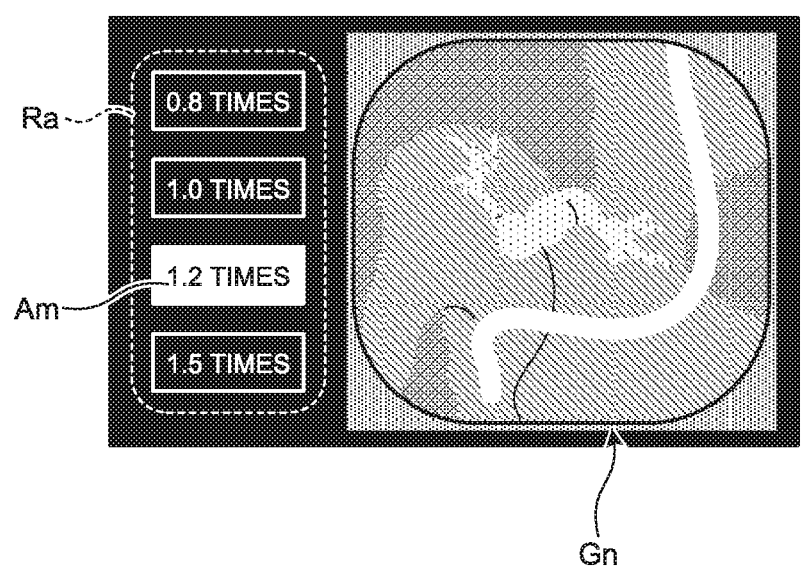

As a result, enlargement-reduction instruction information for instructing enlargement or reduction toward the image signal Gf, is input from the enlargement-reduction instruction input unit 211b into the image processing unit 213 (step S23) via the control unit 212. Based on the enlargement-reduction instruction information, the enlargement-reduction unit 213d generates an X-ray image signal produced by enlarging or reducing the region-of-interest for display, clipped by the region-of-interest clipping unit 213c, and outputs the generated signal to the combining unit 13e (step S24). For example, in a case where an icon image Am that instructs enlargement processing of 1.2 times as illustrated in FIG. 13B is selected by the operator, the enlargement-reduction unit 213d generates an X-ray image signal Gn produced by enlarging the clipped image signal Gf by 1.2 times. Note that it is allowable to configure such that selection icons for enlargement magnification or reduction magnification can be configured to select arbitrary magnification by not only the examples illustrated in FIGS. 13A and 13B but also by displaying a scroll bar on which individual magnifications are movably displayed.

Figure 14:
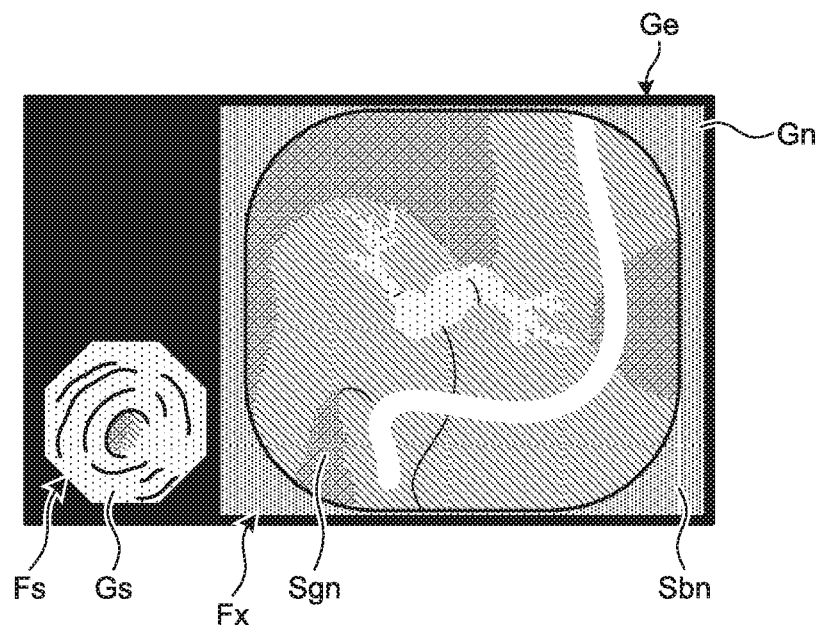
FIG. 14 is a diagram illustrating an exemplary combined image signal generated by the combining unit illustrated in FIG. 9.

Step S25 corresponds to step S6 illustrated in FIG. 2. Subsequently, the combining unit 13e performs combining processing for arranging and combining the X-ray image signal generated by the enlargement-reduction unit 213d and the endoscopic image signal Gs processed by the endoscopic image processing unit 13d, thereby generating a combined image signal (step S26). Step S27 corresponds to step S8 illustrated in FIG. 2. With this processing, for example, as illustrated in FIG. 14, the display device 4 displays a parent-child screen image Ge in which the X-ray image signal Gn (having a picture portion Sgn and a blank portion Sbn) output from the enlargement-reduction unit 213c is arranged within the parent screen Fx and the endoscopic image signal Gs output from the endoscopic image processing unit 13d is arranged within the child screen Fs.

The second embodiment generates and presents the image signal Gw represented by superposing the frame Wx surrounding the initial region-of-interest onto the X-ray image signal Gx. Accordingly, the operator can obtain an image indicating which region corresponds to the picture portion without performing input device operation. The operator can grasp an initial region-of-interest that corresponds to the picture portion by merely confirming the image signal Gw. In the second embodiment, the operator can adjust the size the presented initial region-of-interest to a desired size and can set a region more appropriate for observation, as a region-of-interest for display. The operator can further set the image signal clipped for the region-of-interest for display, to its desired magnification. Therefore, according to the second embodiment, it is possible to generate an image in which the picture portion of the X-ray image signal Gx is represented in the region and size desired by the operator, and thus, to appropriately assist observation of an X-ray image by the operator.

Figure 15:
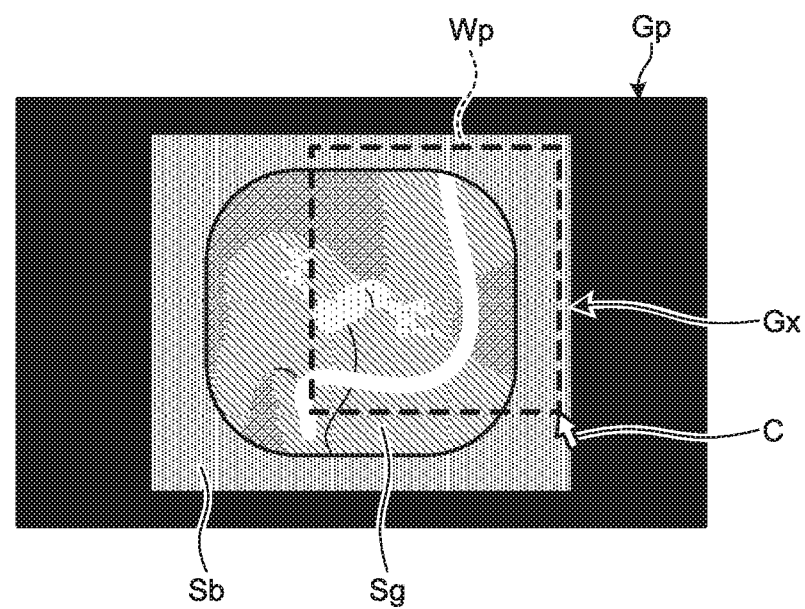
FIG. 15 is a diagram illustrating an exemplary image displayed on a display device in order to set a region-of-interest in an X-ray image signal.

Note that, although the second embodiment describes an example of generating and displaying the image signal Gw represented by superposing the frame Wx surrounding the initial region-of-interest onto the X-ray image signal Gx based on a result of detection by the blank detection unit 13a, the configuration is, of course, not limited to this example. For example, as illustrated in FIG. 15, it is allowable to generate the image signal Gp represented by constantly superposing the frame Wp surrounding a fixed region, onto the X-ray image signal Gx. Even in this case, the processing apparatus 201 performs processing illustrated in steps S21 to S27 in FIG. 12, thereby adjusting the range and size of the region-of-interest for display in the X-ray image signal Gx, and thereafter, displaying a screen image combining the X-ray image signal with the endoscopic image signal, on the display device. In other words, by operating a cursor C on the screen by operating the input device, the operator can set the region-of-interest for display by changing the position and range of the frame Wp to a desired position and range, and can enlarge or reduce the set region-of-interest with a desired magnification.

The first and second embodiments assume that an exemplary X-ray image signal Gx input from the X-ray apparatus 5 is used as an image other than the endoscopic image input from the processing apparatuses 1 and 201. Alternatively, of course, the image may be not only the X-ray image signal but an ultrasound image input from an ultrasound diagnosis apparatus. Moreover in the first and second embodiments, the image processing units 13 and 213 for performing various types of processing, and the display controller 14, illustrated in the above-described FIG. 2 or FIG. 10, and FIG. 12, may be provided not only on the processing apparatuses 1 and 201 of the endoscope system but also on any apparatus as long as it is an apparatus into which the endoscopic image signal, and the X-ray image signal or the ultrasound image signal, are input.

The execution programs for individual processing to be executed in the processing apparatuses 1 and 201 according to the first and second embodiments may be recorded on a computer readable recording medium such as a CD-ROM, a flexible disk, a CD-R and a DVD in a format of a file that can be installed or executed, and may be provided. Alternatively, the program may be stored on a computer connected to a network such as the Internet and may be supplied by downloading the program via the network. It is also allowable to provide or distribute the program via a network including the Internet.

According to some embodiments, provided are a blank detection unit configured to detect a blank portion in a first image signal having a picture portion in which a subject is shown and having a blank portion surrounding the picture portion, a region-of-interest setting unit configured to set an initial region-of-interest corresponding to the picture portion based on the blank portion detected by the blank detection unit, and a region-of-interest image generation unit configured to generate a region-of-interest image signal representing the initial region-of-interest set by the region-of-interest setting unit, thereby to automatically generate an image representing the region-of-interest corresponding to the picture portion. With this configuration, it is possible to reduce burden on an operator in obtaining the image representing the region-of-interest from the input image signal.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus for processing a first image signal including a plurality of pixel signals, the first image signal having a picture portion in which a subject is shown and having a blank portion surrounding the picture portion, the image processing apparatus comprising:
 a processor comprising hardware, wherein the processor is configured to:
  detect, as the blank portion, a portion having uniform color or brightness in the first image signal, by performing at least:
   set a plurality of frames having the same shape but different sizes within a first image created by the first image signal, in a stepwise manner from an outer periphery of the first image; and
   detect the blank portion based on whether or not a part of the plurality of pixel signals belonging to a region outside each of the plurality of similar frames has the uniform color or brightness;
  set an initial region-of-interest corresponding to the picture portion in the first image signal, based on the blank portion detected;
  generate a region-of-interest image signal representing the initial region-of-interest; and
  arrange and combine the region-of-interest image signal and a second image signal of a different type from that of the first image signal, thereby to generate and output a combined image signal,
  wherein the first image signal is an X-ray image signal or an ultrasound image signal, and the second image signal is an endoscopic image signal.

2. The image processing apparatus according to claim 1, wherein the processor is configured to detect the blank portion by performing:
 start detection of the blank portion for a region outside an outermost frame of the plurality of similar frames; and
 iterate the detection of the blank portion for each of the plurality of similar frames while reducing the size in a stepwise manner until the part of the plurality of pixel signals is found to have non-uniform color or brightness.

3. The image processing apparatus according to claim 2, wherein the processor is configured to detect the blank portion by performing, when the part of the plurality of pixel signals is found to have the non-uniform color or brightness for one of the plurality of similar frames, detect, as the blank portion, a region outside an outer frame adjacent to the one of the plurality of similar frames.

4. The image processing apparatus according to claim 1, wherein the processor is configured to detect the blank portion by performing:
 scan the plurality of pixel signals for each horizontal line of the screen representing the first image signal; and
 detect, as the blank portion, the portion having the uniform color or brightness in each horizontal line.

5. The image processing apparatus according to claim 1, wherein the processor is configured to generate the region-of-interest image signal by performing:
 clip the initial region-of-interest from the first image signal; and
 enlarge or reduce the initial region-of-interest clipped from the first image signal depending on a display for the first image signal, thereby to generate the region-of-interest image signal.

6. The image processing apparatus according to claim 1, wherein the processor is configured to generate the region-of-interest image signal by performing:

superpose a frame surrounding the initial region-of-interest onto the first image signal, thereby to generate and output the region-of-interest image signal.

7. The image processing apparatus according to claim 6, wherein the processor is configured to:

receive a change in size of the frame surrounding the initial region-of-interest and receive input of region-of-interest instruction information for designating a region surrounded by the frame of the initial region-of-interest after the size of the frame is changed, as a region-of-interest to be displayed on a display for the first image signal;

clip the region-of-interest from the first image signal based on the region-of-interest instruction information;

receive input of enlargement-reduction instruction information for instructing enlargement or reduction of the region-of-interest clipped; and enlarge or reduce the region-of-interest clipped to generate an image signal based on the enlargement-reduction instruction information.

\* \* \* \* \*